United States Patent [19]

Chynoweth

[11] Patent Number: 4,636,467
[45] Date of Patent: Jan. 13, 1987

[54] MIXED MICROBIAL FERMENTATION OF CARBONACEOUS MATTER TO ROAD DE-ICER

[75] Inventor: David P. Chynoweth, St. Charles, Ill.

[73] Assignee: Institute of Gas Technology, Chicago, Ill.

[21] Appl. No.: 697,253

[22] Filed: Feb. 1, 1985

[51] Int. Cl.$^4$ ............................ C12P 7/54; C12P 7/40; C12P 39/00; C12R 1/145
[52] U.S. Cl. .................................... 435/140; 435/42; 435/136; 435/801; 435/842
[58] Field of Search ................... 435/41, 42, 135, 136, 435/140, 141, 801, 317, 251, 252

[56] References Cited

U.S. PATENT DOCUMENTS

| | | | |
|---|---|---|---|
| 1,602,306 | 10/1926 | Langwell | 435/140 |
| 3,981,803 | 9/1976 | Coulthard | 435/42 |
| 4,022,665 | 5/1977 | Ghosh et al. | |
| 4,318,993 | 3/1982 | Ghosh et al. | |
| 4,377,488 | 3/1983 | Gancy | |
| 4,389,323 | 6/1983 | Gancy | |
| 4,400,285 | 8/1983 | Gancy | |
| 4,405,717 | 9/1983 | Urbas | |
| 4,425,251 | 1/1984 | Gancy | |
| 4,426,308 | 1/1984 | Gancy | |
| 4,430,240 | 2/1984 | Sandvig et al. | |
| 4,430,242 | 2/1984 | Gancy | |
| 4,444,672 | 2/1984 | Gancy | |

FOREIGN PATENT DOCUMENTS 164366 6/1921 United Kingdom .
186572 9/1921 United Kingdom ................. 435/42
572664 10/1945 United Kingdom .
586282 3/1947 United Kingdom .

OTHER PUBLICATIONS

Marynowski et al, 1983, Process Development for Production of Calcium Magnesium Acetate, U.S. Dept. of Transportation, Federal Highway Administration Report No. FHWA/RD-82/145.

Primary Examiner—Raymond N. Jones
Assistant Examiner—Carolyn Paden
Attorney, Agent, or Firm—Thomas W. Speckman

[57] ABSTRACT

A process for production of mixed calcium-magnesium organic acid salts useful for de-icing obtained by anaerobic hydrolysis-fermentation of organic carbonaceous solids by a biologically active mixture of hydrolysis-fermentation anaerobes in which the growth of methanogenic bacteria is suppressed and calcium-magnesium oxygen containing compound is added to the anaerobic digester to control pH and to react with the fermentation acid products to form a mixture of calcium-magnesium organic acid salts. The calcium-magnesium organic acid salts may be readily recovered in solid form for economical utilization in roadway de-icing. The anaerobic digestion is conducted under a naturally obtained mixed microbial population in the presence of the calcium-magnesium oxide containing compound, eliminating the need for pure microbiological strains and sterilization or pasteurization of feed materials.

20 Claims, 1 Drawing Figure

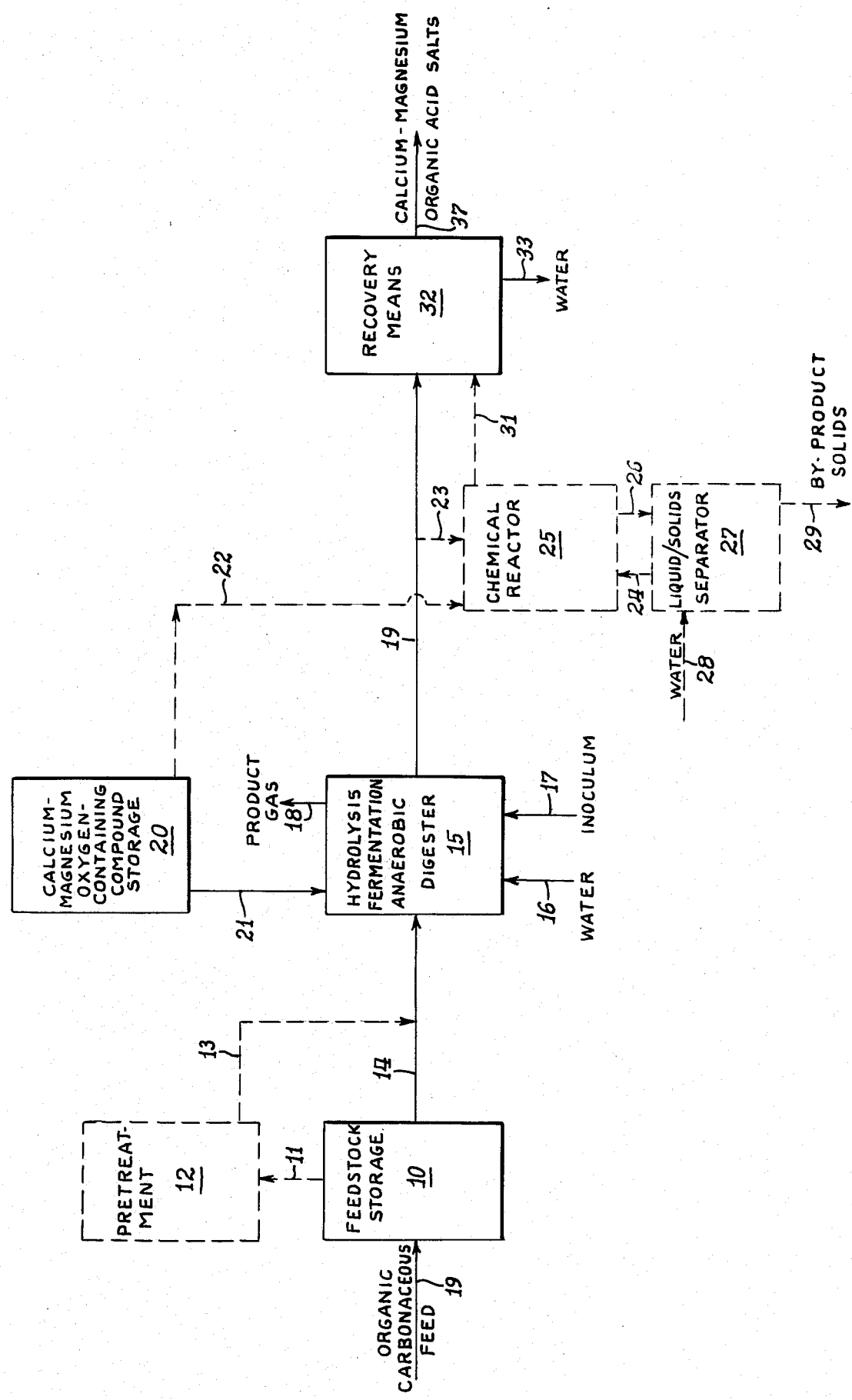

ND MICROBIAL FERMENTATION OF
MIXED MICROBIAL FERMENTATION OF CARBONACEOUS MATTER TO ROAD DE-ICER

BACKGROUND OF THE INVENTION

1. Field of the Invention

This invention relates to a process whereby calcium magnesium salts of acetic acid and other organic acids are produced when biomass, organic waste material and other organic carbonaceous matter is anaerobically digested by a mixed microbial population in the presence of a calcium-magnesium oxygen containing compound.

2. Description of the Prior Art

It is well documented that the de-icing agents currently used, primarily sodium chloride, or rock salt, and smaller quantities of calcium chloride, pose serious health, environmental, and corrosion problems. Sodium chloride and calcium chloride are commonly used because they are the least expensive road de-icing agents available. Sodium chloride, or rock salt, is particularly attractive from a cost standpoint because it exhibits high de-icing efficiency, and it occurs naturally in a substantially pure state and in great abundance. Although the cost of buying and using sodium chloride as a road de-icing agent is exceedingly low, a recent U.S. Environmental Protection Agency study estimated that damage to vehicles, highway structures, flora, fauna and water supplies, inflates the total cost of using rock salt to approximately 14 times the actual cost of mining, distribution and application.

Alternative de-icing agents which are both inexpensive and environmentally safe have been studied. Calcium magnesium acetate (CMA) has been studied and considered by Federal and state agencies as an alternative to sodium chloride or calcium chloride de-icing agents. Laboratory data indicate that CMA has ice melting characteristics similar to those of chloride salts. Because the acetate is biodegradable and calcium and magnesium tend to precipitate in the environment, CMA has fewer potential detrimental health and environmental effects and is also far less corrosive than chloride salts.

Large scale production of CMA is not currently economically feasible. The simplest method of producing CMA is to react dolomitic lime with synthetic acetic acid derived from gas or oil. Synthetic acetic acid is expensive and sufficient quantities are not currently available. For example, if CMA were to penetrate 10 percent of the present rock salt market, a yearly production of 1.5 million tons would be required. Production of 1.5 million tons of CMA would require 1.2 million tons of acetic acid and 600,000 tons dolomitic lime. Dolomitic lime is readily available and relatively inexpensive, but 1.2 million tons of synthetic acetic acid represents twice the 1981 annual production of synthetic acetic acid in the United States. The cost of producing CMA from synthetic acetic acid is approximately 11 to 13 times the cost of rock salt.

In research supported by the Federal Highway Administration and numerous state highway agencies, SRI International developed a fermentation process for the production of CMA. Marynowski, C. W., et al, Process Development for Production of Calcium Magnesium Acetate (CMA); Phase I, SRI International, Report FHWA/RD-82/145, March 1983 and U.S. Department of Transportation, Federal Highway Administration solicitation for study "CMA Manufacture (II); Improved Bacterial Strain for Acetate Production" DTFH61-83-R-00124, June 10, 1983. According to this process, cellulosic matter comprising $C_5$ and $C_6$ sugars is fermented using the bacteria *Clostridium thermoaceticum*. Dolomitic lime is added to the fermentation medium forming calcium and magnesium ions. The cellulosic matter is converted to acetic acid, which reacts with calcium and magnesium ions in situ to form CMA.

This method of producing of CMA, although in theory less expensive than previous methods, suffers serious drawbacks. The fermentation requires a pure culture of *C. thermoaceticum*, which is extremely difficult to maintain. Specialized culture conditions are required to maintain culture purity and to prevent the development of undesirable mutant strains. Even when costly precautionary measure are taken, contamination of the pure bacterial culture by hardier competing bacteria is common.

In addition to the difficulty of the fermentation process itself, the type of raw feed material which can be used for the fermentation is limited and the feedstock must be pretreated or predigested to liberate the $C_5$ and $C_6$ sugars. Ordinarily, this pretreatment entails wet-milling and/or saccharification. Grain, particularly corn, is the preferred feedstock for the fermentation. The cost of the feedstock and its pretreatment contributes significantly to the overall cost of the process. Moreover, *C. thermoaceticum* bacterial populations cannot withstand as low a pH range as is desirable and cannot tolerate the high concentrations of magnesium, calcium and acetate ions which are required to maintain high acetic acid productivity, yield and selectivity. Research is underway to develop a mutant strain of the bacteria *Clostridium thermoaceticum* which can produce high yields of acetic acid under conditions of low pH, and high calcium, magnesium and acetate ion concentrations in the fermentation medium.

A series of patents relating to the production and composition of calcium magnesium acetates and calcium acetates for use as road de-icers has issued recently. Various methods of producing calcium magnesium acetate and calcium acetate are taught in U.S. Pat. No. 4,444,672, teaching a chemical, not biological process for manufacturing a calcium acetate salt and teaching the addition of an inert anti-slip solid; U.S. Pat. No. 4,425,251, disclosing mixed dry chemical formulations of a stable acid-acetate salt and a chemical base which reacts when it contacts snow or ice; U.S. Pat. No. 4,400,285, teaching a chemical composition of calcium oxide and calcium magnesium acetate as a de-icing agent; U.S. Pat. No. 4,389,323, teaching a chemical, not biological process for manufacturing two different grades of CMA; U.S. Pat. No. 4,430,242, disclosing a chemical, not biological process for producing calcium acetate and calcium acid-acetate in a rotary kiln-type reactor, with unreacted raw limestone serving as a traction agent; U.S. Pat. No. 4,426,308, teaching a chemical, not biological process for producing calcium acetate containing solution and its conversion to solid flakes; and U.S. Pat. No. 4,377,488, teaching a chemical, not biological process for making calcium acetate de-icing agents.

U.S Pat. No. 4,405,717 teaches the recovery of acetic acid from dilute aqueous solutions. This patent also teaches the production of calcium acetate by the fermentation of glucose using a pure culture of *Clostridium thermoaceticum*.

British Pat. No. 164,366 teaches the fermentation of cereals in the presence of calcium carbonate to form calcium acetate. British Pat. Nos. 572,664 and 586,282 both describe fermentation in the presence of calcium carbonate to form a water soluble acetate. U.S. Pat. No. 4,430,240 teaches the production of calcium and magnesium acetates from waste products, such as sawdust, by reaction with alkaline earth metal oxides or hydroxides at elevated pressure and temperature.

Two phase anaerobic digestion processes in which biomass is converted to methane gas are taught in U.S. Pat. Nos. 4,022,665 and 4,318,993. In the first stage, or "acid phase" digestion, carbonaceous biomass or organic waste material is converted to primarily soluble volatile fatty acids with the formation of some product gas.

SUMMARY OF THE INVENTION

It is an object of the present invention to provide a process for producing calcium-magnesium organic acid salts for use as a de-icer which process is suitable for use in large scale operations, is energy efficient, and economically feasible.

It is a further object of this invention to provide an inexpensive source of organic acids, such as acetic acid, by means of a fermentation process capable of utilizing a variety of carbonaceous feedstocks, including biomass, peat, organic waste material and other carbonaceous matter.

It is yet another object of this invention to provide hydrolysis-fermentation of raw feedstock, thereby eliminating any requirement for pretreatment or saccharification of the feedstock.

It is still another object of this invention to provide hydrolysis-fermentation of raw feedstock in the presence of a calcium-magnesium oxygen containing compound to promote the in situ formation of mixed calcium-magnesium organic acid salts, generally predominately CMA.

It is a further object of this invention to produce calcium-magnesium organic acid salts during a hydrolysis-fermentation process using a mixed microbial population comprising primarily acid forming bacteria eliminating requirements for feed sterilization or pasteurization and pure culture maintenance.

According to the process of the present invention, raw organic carbonaceous feedstock is fermented by a mixed hydrolysis-fermentation microbial population comprising primarily acid forming bacteria, to produce volatile fatty acids, which may be primarily acetic acid. The mixed microbial population eliminates the need of prior processes to maintain a pure culture and does not require feed sterilization or pasteurization. Calcium-magnesium oxygen containing compound selected from the group consisting of carbonate, oxide, hydroxide, and mixtures thereof, may be introduced directly into the fermentation vessel and combines with free organic acid to form calcium and magnesium organic acid salt, normally predominately acetate. The other acids present also form calcium-magnesium salts resulting in a mixed organic acid salt composition. The fermentation medium containing CMA and other organic acid salts is subsequently separated from the liquid medium and when dried and crushed, is suitable for use as a road de-icer.

Any organic carbonaceous material which is susceptible to anaerobic biodegradation by the mixed hydrolysis-fermentation microbial population may be used as feedstock. Suitable organic carbonaceous feedstocks include biomass, crop residue, peat, wood, and municipal and industrial wastes, such as sewage sludge. Mechanical degradation of the feedstock to a conveniently digestable size may be necessary, depending upon the organic feedstock utilized. Chemical or physical pretreatment of the feedstock is not required, but physical, chemical, or enzymatic pretreatment may be employed to accelerate reaction kinetics. Pretreatment suitable for use in the process of this invention is less severe than required for other digestion processes. Organic carbonaceous feed may be continuously or intermittently introduced into an anaerobic digester, wherein the microbial population comprises mixed hydrolysis-fermentation species which convert the organic substrate to low molecular weight aldehyde and alcohol intermediates, and organic acids such as acetic acid, propionic acid and butyric acid. Suitable anaerobic digesters, growth medium and operating conditions are well known to the art. The "acid phase" of the two phase anaerobic digestion processes described in U.S. Pat. Nos. 4,022,665 and 4,318,993 provide exemplary operating conditions with modifications noted below to suppress methanogenic bacteria. The process of this invention is not limited to the systems of these patents.

Mixed hydrolysis-fermentation microbial species facilitate each step in the conversion of the organic carbonaceous solids to the desired volatile fatty acids. The microbial population in the anaerobic digester of this invention comprises numerous species of hydrolysis-fermentation bacteria so that conversion of organic substrate to organic acids and their intermediates occurs continuously and simultaneously. Digester conditions may be adjusted to favor the growth of bacteria which convert intermediates to acetic acid, the desired product. Other acids, such as lactic and succinic acid may also be formed during the digestion, and processed along with the other fermentation products. The volatile organic acid product of the anaerobic digestion remains solubilized in the liquid digester contents. It is desired to suppress growth of methanogenic bacteria which may be achieved by utilization of gases produced during the digestion, primarily carbon dioxide and molecular hydrogen, which may be continuously or frequently withdrawn from the digester, the digester may be subjected to periodic oxygenization, and/or a low hydraulic retention time may be maintained. Inhibitors may also be used to enrich the desired microbial population of organic acid forming bacteria.

Calcium-magnesium oxygen containing compound selected from the group consisting of carbonate, oxide, hydroxide, and mixtures thereof, such as dolomite ($CaCO_3 \cdot MGCO_3$) or dolomitic lime ($CaO \cdot MgO$) may be introduced directly into the anaerobic digester and/or may be combined with the solubilized digester products in a separate vessel. Introduction of the calcium-magnesium oxygen containing compound directly into the digester medium provides in situ formation of organic acid calcium and magnesium salts avoiding the necessity of volatile acid recovery, and provides relatively easy salt recovery. The low solubility of the carbonate and oxide in the aqueous digester medium enables it to act as a buffer for the digester medium, thus additionally providing pH control. In the aqueous medium, the carbonate and oxide salts form hydroxides for reaction.

CMA may be formed by the reaction of acetic acid (CH₃COOH) and the calcium-magnesium hydroxides as follows:

and

Although acetic acid may be the principal solubilized product of the anaerobic digestion according to this invention, other volatile fatty acids, particularly propionic and butyric acids, may be produced during the fermentation and may also react with the calcium-magnesium oxygen containing compound to form their calcium and magnesium salts. Suppression of the secondary reactions is not critical because the calcium and magnesium salts of other organic acids are non-toxic, and are similar to acetate salts in their de-icing properties.

Calcium and magnesium salts of mixed organic acids, primarily calcium and magnesium acetate, remain solubilized in the anaerobic digestion medium, and may be removed from the anaerobic digester and conveyed to a chemical reactor vessel where additional calcium-magnesium oxygen containing compound may be added to promote more complete conversion of the mixed organic acids to their calcium and magnesium salts. Solids suspended in the digester medium may be separated and may be subsequently dried and conveyed to by-product storage or utilization.

The aqueous supernatant medium, having a high concentration of dissolved organic acid calcium and magnesium salts, may be transferred to a recovery means, such as a crystallizer wherein excess liquid may be removed by evaporation, solvent extraction or other crystallizing process and the calcium-magnesium salts of organic acids are crystallized. The salts may then be finished by further drying and crushed to provide a mixed calcium-magnesium organic acid salt product which is suitable for road de-icing while providing the advantages of pure CMA.

Production of CMA and other calcium-magnesium organic acid salts by the process of this invention results in a significant cost reduction due to broader feed capability, reduction in the need for chemical or physical pretreatment, and the elimination of the requirement for a pure microbial culture.

BRIEF DESCRIPTION OF THE DRAWING

These and other objects, advantages and features of this invention will be apparent from the description, together with the figure which shows a highly schematic block diagram of the process of this invention, with dashed lines representing alternative embodiments.

DESCRIPTION OF THE PREFERRED EMBODIMENTS

The process of this invention is applicable to many types of organic feed materials. The term "organic carbonaceous feed material" as used in this disclosure and the appended claims means any type of organic carbonaceous material such as sewage sludge, municipal waste, animal waste, industrial waste, forestry waste, agricultural waste, water and land plants, peat, and other highly organic carbonaceous matter. Mechanical degradation of the feed material may be required to achieve the wide range of particle sizes suitable for use in anaerobic digestion according to this invention. Such mechanical degradation is well known to the art. The process of this invention may be utilized without any chemical or physical pretreatment of the organic carbonaceous substrate, but such pretreatment may be employed if the organic carbonaceous feedstock is recalcitrant to hydrolysis-fermentation anaerobic digestion. Acid or alkaline hydrolysis or enzymatic pretreatment as generally known to the art may be utilized to prepare organic carbonaceous feedstock for digestion. Pretreatment utilized in the process of this invention is considerably less severe than required for other digestion processes. Pretreatment of organic feedstock primarily affects reaction kinetics, and therefore reaction rates may be enhanced using various pretreatment techniques. Organic carbonaceous feedstocks which are readily reactable in the mixed anaerobic hydrolysis-fermentation environment of this invention do not require pretreatment.

As shown in the figure, organic carbonaceous feed may be supplied by supply means 19 to any suitable feedstock storage means 10 and conveyed from organic feedstock storage means 10 through delivery means 14 to hydrolysis-fermentation anaerobic digester 15. In an alternative embodiment, organic feedstock from storage means 10 may be conveyed through conduit 11 to pretreatment means 12, where the feedstock may undergo suitable chemical, physical, or enzymatic pretreatment and pretreated feedstock may be conveyed through conduit 13 to delivery means 14 or hydrolysis-fermentation anaerobic digester 15. The pretreatment which may be advantageous in the process of this invention will generally be much less severe than the pretreatments required with prior processes.

Organic carbonaceous feed may be continuously or intermittently introduced into hydrolysis-fermentation anaerobic digester 15 at a rate of about 0.2 to 10 pounds of total organics per cubic foot per day, depending upon the type of organic feedstock being processed. Hydrolysis-fermentation in digester 15 is initiated with a mixed hydrolysis-fermentation microbial inoculum which can be adapted, through natural selection, to degrade a wide variety of biomass and waste feedstocks. Suitable inoculum for introduction through inoculum supply conduit 17 is desirably a broad spectrum inoculum of highly mixed bacteria capable of anaerobically degrading diverse organic carbonaceous substrate and may be derived from sources such as anaerobic lake sediments, cow rumen, and the like. Each of the numerous species contained therein accomplishes the biodegradation of organic substrate to volatile fatty acids, or an aldehyde or alcohol intermediate. The mixed anaerobic culture converts a broader spectrum of substrates including lipids and proteins. The mixed anaerobic culture avoids the expensive maintenance of a pure culture, as required by prior processes, and avoids the necessity of feed sterilization or pasteurization. The organic carbonaceous feed material utilized in the process of this invention contains a relatively high lignin content which is not biodegraded and is useful for energy production or for its chemical value. A review of the microbiology of anaerobic digestion is set forth in Anaerobic Digestion, 1; The Microbiology of Anaerobic Digestion, D. F. Toerien and W. H. J. Hattingh, Water Research, Vol. 3, pages 385–416, Pergamon Press (1969). As set forth in that review, the principal suitable hydrolysis-fermentation bacteria include species from genera including Aerobacter, Aeromonas, Alcaligenes, Bacillus, Bacteroides, Clostridium, Escherichia, Klebsiella, Leptospira, Micrococcus, Neisseria, Paracolobactrum, Proteus, Pseudomonas, Rhodopseudomonas, Sarcina, Serratia, Streptococcus and Streptomyces. *C. thermoaceticum* will not be a dominant species in this mixed culture. Methane forming bacteria are desirably suppressed and known chemical inhibitors may be used, such as chloroform or carbon tetrachloride. Slight oxygenation of the digester and reduced hydraulic retention time aid in suppression of the slow growing methanogenic bacteria. Nutritional balance and adjustments may be made as is known to the art to favor hydrolytic action. The contents of hyrolysis-fermentation anaerobic digester 15 may be continuosuly or intermittently agitated to promote vigorous digestion, but unmixed digesters may also be used.

The organic carbonaceous substrate in anaerobic digester 15 may be subjected to anaerobic hydrolysis-fermentation of mesophilic temperatures, from about 15° to about 45° C., or at thermophilic temperatures, from about 45° to about 70° C. Water and/or support medium, including nutritional materials, is delivered to digester 15 through conduit 16. Suitable support medium is well known to the art.

The pH in digester 15 is maintained below about 8, preferably between about 4 and about 7. The time detention of organic substrate in digester 15 varies widely according to the type of organic substrate being digested. For example, for organic substrate comprising primarily wood chips, detention times of about 30-60 days are suitable; relatively insoluble particulate solids such as biomass, require detention times of about 15-30 days, and soluble and finely divided substrate, such as sewage sludge, requires a detention time of about 4 hours to about 5 days. The pH may be varied to favor particular desired products by enrichment of desired microorganisms.

Methanogenic microorganisms may be suppressed by low average hydraulic retention times of less than about 7 to 8 days for mesophilic digestion and less than about 3 to 4 days for thermophilic digestion. Longer retention times may be used in conjunction with other methanogenic inhibitors. Removed liquid and/or solids may be recycled to the digester following treatment, or digester may be treated directly, such as oxygenation, heat chemical inhibitors, such as chloroform, to reduce methanogenic bacteria. Periodic aeration of the digester, producing oxygenization, may also be practiced to suppress methanogenic microorganisms.

The biodegradable portion of the organic carbonaceous substrate is converted to organic acids, primarily acetic acid, and alcohol and aldehyde intermediates, which remain solubilized in the liquid digester medium, and gaseous products, principally hydrogen and carbon dioxide. Gaseous products may be withdrawn continuously or intermittently through gas withdrawal conduit 18. Frequent or continual removal of moleculor hydrogen from digester 15 will promote the formation of calcium and magnesium acetate in preference to calcium and magnesium salts of higher molecular weight fatty acids.

In a preferred embodiment, the calcium-magnesium oxygen containing compound is conveyed from storage means 20 and introduced through conduit 21 directly into anaerobic digester 15. This arrangement promotes in situ formation of calcium-magnesium organic acid salts, and avoids the necessity of a separate organic acid recovery unit. Furthermore, the addition of the calcium-magnesium oxygen containing compound provides a convenient pH control mechanism. Because of their low solubility these compounds act as a buffer in the digester medium and the slightly acidic desired pH range is more readily maintained. Additionally, the calcium-magnesium oxygen containing compounds react with the organic acids in the digester to form the desired calcium and magnesium salts of the organic acids. Acetic acid is usually the principal solubilized product of the anaerobic digestion, and consequently CMA is the principal product. The calcium and magnesium salts of the organic acids remain solubilized in the digester medium. The quantity of calcium-magnesium oxygen containing compound added is the amount necessary for the desired organic acid salt formation while maintaining the desired pH for enhancement of the mixed anaerobic hydrolysis-fermentation.

Product solubilized in digester medium suspension is withdrawn from digester 15 through digester product conduit 19 and may be conveyed directly to recovery means 32, or alternatively, may be conveyed in total or in part through conduit 23 to chemical reactor 25. Calcium-magnesium oxygen containing compound from storage means 20 may be conveyed through conduit 22 to chemical reactor 25 to promote more complete conversion to the desired organic acid salts. High solids portions of the digester medium suspension may be withdrawn from chemical reactor 25 and conveyed through liquid/solids transfer conduit 26 to liquid/solids separator 27 wherein solids and liquids may be separated by any suitable means known to the art. By-product solids, usually high in lignin content, may then be conveyed through solids conduit 29 for storage or utilization. Separated liquids may be returned to chemical reactor 25 through liquid conduit 24, together with water which may be added through conduit 28. Supernatant product liquid may be conveyed from chemical reactor 25 through conduit 31 to recovery means 32.

Recovery means 32 may comprise any suitable method for recovery of the calcium-magnesium organic acid salts in solid form useful for de-icing agents. For example, various methods for acid salt concentration by crystallization, evaporation, and membrane separation are known. Liquids may be separated by evaporation in a crystallizer of recovery means 32 and withdrawn through liquid discharge conduit 33 and the solid calcium-magnesium organic acid salts in solid form further dried, as desired, and crushed and sized for removal by conduit 37 in suitable form for use as a de-icing composition.

The process of this invention provides an economically attractive method for production of environmentally favorable de-icing agents for use on roadways. The process utilizes naturally obtained mixed cultures for anaerobic digestion of a wide variety of inexpensive organic carbonaceous feedstocks with the in-situ formation of mixed calcium-magnesium organic acid salts which may be easily recovered from the liquid medium.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for production of mixed calcium-magnesium organic acid salts useful for de-icing, said process comprising:
   adding organic carbonaceous solids to a hydrolysis-fermentation anaerobic digester;
   conducting anaerobic hydrolysis-fermentation of said carbonaceous solids by a biologically active mixture of hydrolysis-fermentation anaerobes comprising primarily acid-forming bacteria while suppressing growth of methanogenic bacteria in said digester to promote the production of fermentation acid products;
   adding calcium-magnesium oxygen containing compound to said digester in a quantity sufficient to maintain said digester pH at about 4 to about 7 and to react said calcium-magnesium oxygen containing compound with substantially all said fermentation acid products to form a mixture of calcium-magnesium organic acid salts; and
   recovering said calcium-magnesium organic acid salts in solid form.

2. The process of claim 1 wherein said calcium-magnesium oxygen containing compound is selected from the group consisting of carbonate, oxide, hydroxide and mixtures thereof.

3. The process of claim 1 wherein said calcium-magnesium oxygen containing compound comprises calcium-magnesium carbonate.

4. The process of claim 1 wherein said calcium-magnesium oxygen containing compound comprises calcium-magnesium oxide.

5. The process of claim 1 wherein said organic carbonaceous solids are selected from the group consisting of biomass, crop residue, peat, wood, municipal waste, industrial waste, and mixtures thereof.

6. The process of claim 1 wherein said biologically active mixture of hydrolysis-fermentation anaerobes is achieved by natural selection and growth of a mixed inoculum under conditions suppressing growth of methanogenic bacteria.

7. The process of claim 1 wherein said suppressing growth of methanogenic bacteria is achieved by a low hydraulic retention time.

8. The process of claim 1 wherein said suppressing growth of methanogenic bacteria is achieved by chemical inhibitors.

9. The process of claim 1 wherein said anaerobic hydrolysis-fermentation is carried out under mesophilic conditions for average hydraulic retention times of less than about 7 to 8 days.

10. The process of claim 1 wherein said anaerobic hydrolysis-fermentation is carried out under thermophilic conditions for average hydraulic retention times of less than about 3 to 4 days.

11. The process of claim 1 wherein fermentation acid products are removed from said digester and passed to a chemical reactor for reaction with said calcium-magnesium oxygen containing compound to form additional calcium-magnesium organic acid salts.

12. The process of claim 1 wherein calcium-magnesium organic acid salts are recovered by crystallization.

13. The process of claim 1 wherein said calcium-magnesium oxygen containing compound is selected from the group consisting of carbonate, oxide, hydroxide, and mixtures thereof; said biologically active mixture of hydrolysis-fermentation anaerobes is achieved by natural selection and growth of a mixed inoculum under conditions suppressing growth of methanogenic bacteria; and fermentation acid products are removed from said digester and passed to a chemical reactor for reaction with said calcium-magnesium oxygen containing compound to form additional calcium-magnesium organic acid salts.

14. The process of claim 13 wherein the principal product is calcium-magnesium acetate.

15. In a process for anaerobic hydrolysis-fermentation of organic carbonaceous solids, the improvement comprising; conduct of said hydrolysis-fermentation by a biologically active mixture of hydrolysis-fermentation anaerobes comprising primarily acid-forming bacteria while suppressing growth of methanogenic bacteria to promote production of fermentation acid products and in the presence of calcium-magnesium oxygen containing compound to react with substantially all said fermentation acid products to form in-situ a mixture of calcium-magnesium organic acid salts.

16. In the process of claim 15 wherein said calcium-magnesium oxygen containing compound is selected from the group consisting of carbonate, oxide, hydroxide and mixtures thereof.

17. In the process of claim 15 wherein said calcium-magnesium oxygen containing compound comprises calcium-magnesium carbonate.

18. In the process of claim 15 wherein said calcium-magnesium oxygen containing compound comprises calcium-magnesium oxide.

19. In the process of claim 15 wherein said biologically active mixture of hydrolysis-fermentation anaerobes is achieved by natural selection and growth of a mixed inoculum under conditions suppressing growth of methanogenic bacteria.

20. In the process of claim 15 wherein the principal product is calcium-magnesium acetate.

* * * * *